(12) United States Patent
Bary

(10) Patent No.: US 7,456,328 B2
(45) Date of Patent: Nov. 25, 2008

(54) BLENDING PROCESSES AND SYSTEMS

(75) Inventor: Michael R. Bary, The Woodlands, TX (US)

(73) Assignee: NGL Solutions, LLC, Conroe, TX (US)

( * ) Notice: Subject to any disclaimer, the term of this patent is extended or adjusted under 35 U.S.C. 154(b) by 610 days.

(21) Appl. No.: 10/919,056

(22) Filed: Aug. 16, 2004

(65) Prior Publication Data

US 2006/0035381 A1    Feb. 16, 2006

(51) Int. Cl.
    *C10L 3/00*    (2006.01)
    *G01N 35/08*   (2006.01)
(52) U.S. Cl. .................... 585/6; 585/1; 436/55
(58) Field of Classification Search .......... 585/1, 585/302, 955, 720, 922, 6, 14; 700/265; 366/163.2; 436/55
    See application file for complete search history.

(56) References Cited

U.S. PATENT DOCUMENTS

| | | | | |
|---|---|---|---|---|
| 3,263,491 | A | * | 8/1966 | Brown et al. .............. 73/64.46 |
| 4,494,209 | A | * | 1/1985 | Agarwal ..................... 700/265 |
| 4,979,091 | A | | 12/1990 | Albers |
| 5,050,064 | A | | 9/1991 | Mayhew |
| 5,365,435 | A | | 11/1994 | Stephenson |
| 5,570,743 | A | | 11/1996 | Padgett et al. |
| 5,600,134 | A | * | 2/1997 | Ashe et al. ................ 250/252.1 |
| 5,629,863 | A | | 5/1997 | Palozzi et al. |
| 5,656,313 | A | | 8/1997 | Gibney et al. |
| 5,671,153 | A | | 9/1997 | Brinkmeyer et al. |
| 5,871,634 | A | | 2/1999 | Wiehe et al. |
| 6,186,193 | B1 | | 2/2001 | Phallen et al. |
| 6,235,955 | B1 | | 5/2001 | Yao et al. |
| 6,253,779 | B1 | | 7/2001 | Nanaji et al. |
| 6,436,863 | B2 | | 8/2002 | Wu et al. |
| 6,732,796 | B2 | | 5/2004 | Vinegar et al. |
| 2003/0111488 | A1 | * | 6/2003 | Schell et al. .................. 222/64 |
| 2004/0240311 | A1 | * | 12/2004 | Hashiba ..................... 366/101 |

OTHER PUBLICATIONS

Perry, R.H.; Green. D.W., Perry's Chemical Engineers' Handbook, 1997, McGraw-Hill, 7th Edition, p. 2-50.*

* cited by examiner

*Primary Examiner*—Walter D Griffin
*Assistant Examiner*—Natasha Young
(74) *Attorney, Agent, or Firm*—Jeffrey L. Wendt; Pramudji Wendt & Tran, LLP

(57) ABSTRACT

Processes and systems are provided for monitoring and blending a first stream and a second stream to produce a third stream of desired compositional characteristics. The processes and systems are found to be particularly useful for the blending of two or more hydrocarbon streams to economically produce a targeted hydrocarbon product stream meeting prescribed compositional specifications. Specifically, the processes and systems are found to be especially useful to blend a propane containing stream, having a vapor pressure lower than the vapor pressure of a targeted vapor pressure for a propane product, with an ethane containing stream. The blending processes and systems allow for production of an "on-spec" propane product stream while at the same time maximizing the value of the ethane stream. The processes and systems may incorporate continuous real-time analysis and flow control of the various streams to effectuate precise control the blending processes.

20 Claims, 2 Drawing Sheets

BLENDING PROCESSES AND SYSTEMS

FIELD OF THE DISCLOSURE

This disclosure relates to processes and systems for monitoring and blending at least two liquid or gaseous streams, or combinations thereof, to produce a third liquid or gaseous stream having targeted compositional characteristics based upon relative proportions of the first and second streams in the third blended stream.

BACKGROUND INFORMATION

Numerous systems are known for the production of blended streams. For example, U.S. Pat. No. 6,186,193 discloses a method and apparatus providing for the continuous stream blending of two or more liquid streams. Each liquid stream is synchronously dosed in a mass ratio to a common mixing point. The flow of each stream is controlled by a digital on-off control. Each dose stream flow is produced and measured by a four element apparatus consisting of a servo motor and controller, a precision positive displacement pump, a mass meter, and a stream flow shut-off device. The servomotor and controller establish and control a periodic and intermittent flow rate required to displace a defined mass dose in a precisely defined flow interval. The system is said to be useful for blending components to produce a variety of industrial and commercial products.

U.S. Pat. No. 6,253,779 discloses a system for blending two-blend components to form a blended product. The system includes a first supply line for supplying a first blend component at a first flow rate and a second supply line for supplying a second blend component at a second flow rate. The first supply line and the second supply line intersect to form a blended product line. The system also includes a blended product measuring device positioned in the blended product line for measuring the flow rate of the blended product and an auxiliary measuring device positioned in the first supply line for measuring the flow rate of the first blend component. The system is said to be useful for blending products streams such as two gasoline streams having different octane levels to produce a third stream having yet another octane level.

U.S. Pat. No. 4,979,091 discloses a system for the blending of various streams having various flow rates and various concentrations. It is disclosed that the system continuously manipulates the composition of one of the streams being blended in such a manner that a blended product is provided which has a specified composition. The system is said to be useful for controlling the purity of the propane product from a refinery and for the continuous control of a gas or liquid blending where it is desired to meet a product specification by blending streams of various flow rates and composition. The patent discloses a system in which the composition of a blended propane product is monitored and feedback control is provided to control a de-ethanizer tower to increase or decrease the ethane content in one of the streams blended to produce the propane product.

U.S. Pat. Nos. 5,629,863; 5,871,634; 6,235,955; 6,436,863; and 6,732,796 disclose exemplary other known blending systems for production of various blended products.

BRIEF DESCRIPTION OF THE DISCLOSURE

This disclosure relates to processes, equations, and systems for monitoring and blending at least a first stream and a second stream to produce a third stream of desired compositional characteristics. The processes, equations, and systems are found to be particularly useful for blending two or more hydrocarbon streams to economically produce a targeted product stream meeting prescribed compositional or physical properties specifications. Specifically, in one embodiment, the processes, equations, and systems are found to be especially useful to blend a propane containing stream, having a vapor pressure lower than the vapor pressure of a targeted vapor pressure for a propane product, with an ethane containing stream. The blending processes, equations, and systems allow for production of an "on-spec" propane product stream while at the same time maximizing the value of the ethane-containing stream. The processes and systems may incorporate continuous real-time analysis and flow control of the various streams to effect precise control of the blending processes.

DETAILED DESCRIPTION OF THE DISCLOSURE

Figure 1:
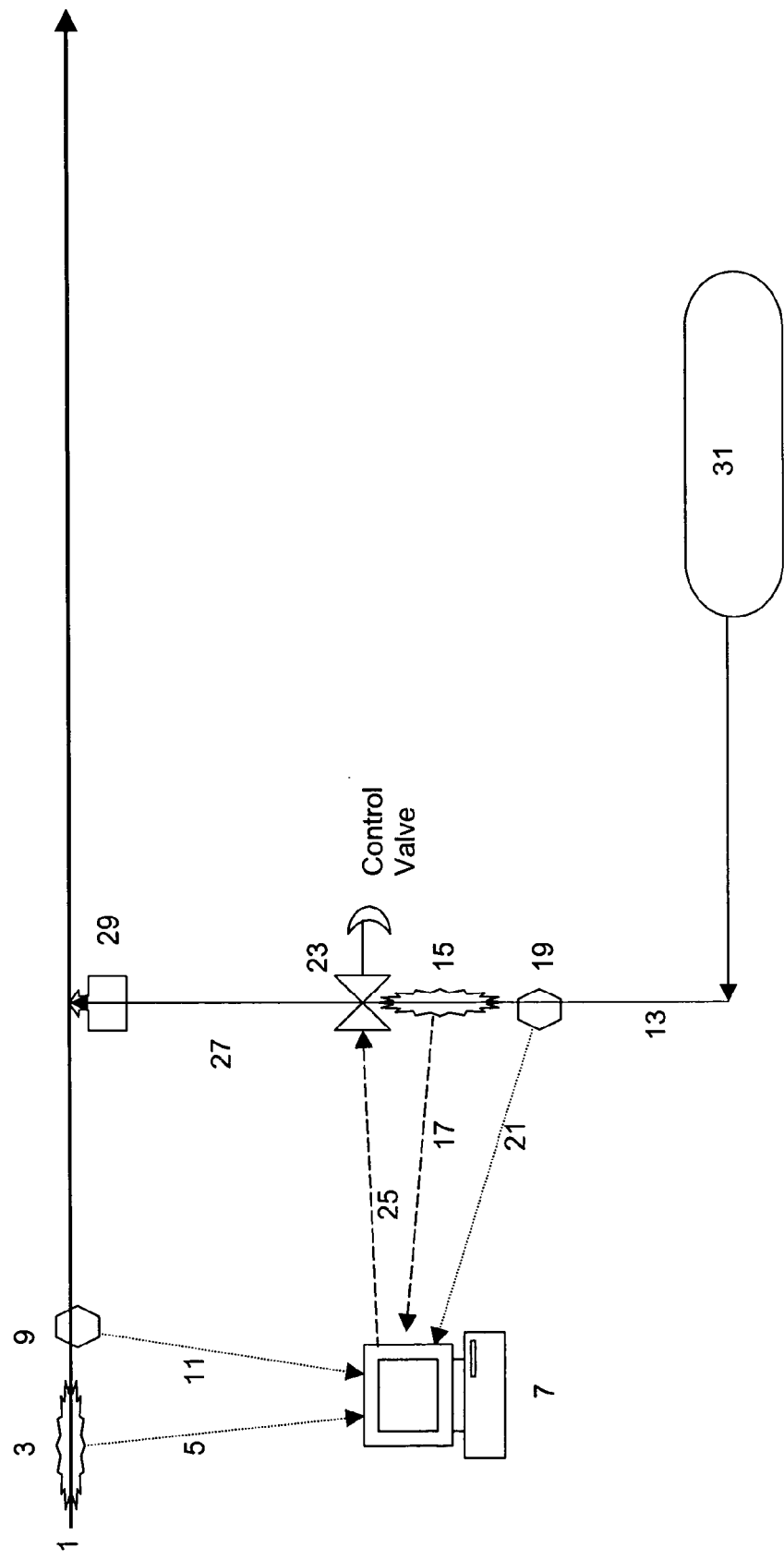
FIG. 1 is a schematic representation of an embodiment of the processes and systems described herein.

This disclosure relates to processes and systems for monitoring and blending a first stream and a second stream to produce a third stream of desired compositional characteristics. The processes and systems described herein may be used to blend a variety of liquid and gaseous streams, and combinations thereof, to produce a blended liquid or gaseous stream having a composition different than any of the streams combined to produce the blended stream. The processes and systems described herein may be used to produce a wide range of industrial and commercial blended streams. The processes and systems described herein are discussed primarily in the context of blending liquid streams, however, as noted above, it is understood that the processes and systems described herein are applicable to blending multiple gaseous streams as well as liquid and gaseous streams.

In one embodiment, the processes and systems are found to be particularly useful for the blending of two or more hydrocarbon streams to economically produce a targeted product stream meeting prescribed compositional specifications. In certain embodiments, the hydrocarbon streams comprise at least 90 volume percent hydrocarbons component(s). In another embodiment, the targeted product stream is an LPG propane product stream meeting mandated product specifications. In certain embodiments, the targeted product stream, or third stream, comprises less than 95 volume percent propane and at least 4 volume percent ethane.

Conventional refinery distillation processes produce propane product streams with high propane content. For example, conventional refinery produced propane streams may have propane concentrations nearing 100 liquid volume percent, with vapor pressures as low as 174 psig @ 100° F. (1.19 MPag at 37.7° C.). These propane product streams are sold into an extensive distribution network through which significant volumes of the propane product streams are sold as LPG products. In the United States and elsewhere, the LPG product streams are sold under specification standards mandated by contract or industry bodies. For example, in the United States, HD-5 propane must have a vapor pressure not to exceed 208 psig at 100° F. (1.43 MPag at 37.7° C.) and a propane concentration of at least 90 liquid volume percent. A variety of different specifications exist for different LPG product streams as well as for other types of products sold commercially.

With respect to LPG product streams, ethane, propane, propylene and iso-butane content are the primary components that determine vapor pressure. A pure propane stream has a vapor pressure of 174 psig at 100° F. (1.19 MPag at 37.7° C.). LPG product streams, available or sold commercially, because of lighter hydrocarbon components, have vapor pressures between 174 psig at 100° F. (1.19 MPag at 37.7° C.) and 208 psig at 100° F. (1.43 MPag at 37.7° C.). Significantly, most LPG product streams available from refineries typically have vapor pressures less than 190 psig at 100° F. (1.31 MPag at 37.7° C.).

Because many LPG product streams produced at refineries have vapor pressures significantly less than the permitted maximum pressures for LPG product streams, as well as propane concentrations higher than required for LPG product streams, it has been determined that a precise amount of a stream containing ethane, and optionally other components, may be blended into the LPG product streams. This blending produces a product stream that still meets prescribed LPG product streams vapor pressure and minimum propane concentration specifications. The precise blending of an ethane stream into the LPG product stream, in accordance with the systems and processes described herein, effectively allows an economical upgrade of the typically lower value ethane product to a higher value propane product. The blending also creates a productive use of ethane products that may otherwise be disposed of as waste streams.

In one embodiment, the systems and processes described herein use volume and composite analysis to calculate a blend ratio of a predominately propane stream and a predominately ethane stream sufficient to produce a propane stream containing a volume of ethane necessary to create a blended propane stream with a targeted vapor pressure of 208 psig at 100° F. (1.43 MPag at 37.7° C.), or other targeted vapor pressure propane. Such systems and processes using the same such volumes and compositions also limit the blend ratio to meet minimum propane liquid volume percent requirements of the controlling specifications although at reduced vapor pressures.

In certain embodiments, a computer control system actuates a control valve allowing a precise volume of ethane to flow into the propane stream. The processes and systems may incorporate continuous real-time analysis and flow control of the various streams to effectuate precise control of the blending processes.

An exemplary process in accordance with this disclosure is the blending of a first stream comprising at least 90 volume percent propane and a second stream comprising at least 60 liquid percent ethane to produce a third stream that is a product stream having a targeted vapor pressure range of about 174 psig at 100° F. (1.19 MPag at 37.7° C.) to about 208 psig at 100° F. (1.43 MPag at 37.7° C.), as may be limited by minimum propane liquid volume percent specifications. In other embodiments, the first stream comprises at least 90 liquid volume percent propane and the second stream comprising at least 60 volume percent ethane. In certain embodiments, the first stream has a vapor pressure of about 170 psig at 100° F. (1.17 MPag at 37.7° C.) to about 186 psig at 100° F. (1.28 MPag at 37.7° C.) and the second stream has a vapor pressure of about 392 psig at 100° F. (2.7 MPag at 37.7° C.) to about 785 psig at 100° F. (5.41 MPag at 37.7° C.). In still other embodiments, a first stream comprising propane and a second stream comprising ethane may be blended to produce a third stream that is a product stream having a targeted vapor pressure range of about 198 psig at 100° F. (1.36 MPag at 37.7° C.) to about 208 psig at 100° F. (1.43 MPag at 37.7° C.).

In one embodiment, such a third stream may be a LPG propane product. In this embodiment, the processes and systems described herein are useful to blend a propane containing stream, having a vapor pressure lower than the vapor pressure of a targeted vapor pressure for a propane product, with an ethane containing stream. The blending processes and systems allow for production of an "on-spec" propane product stream while at the same time maximizing the value of the ethane stream.

The processes and systems may incorporate continuous real-time analysis and flow control of the various streams to effectuate precise control of the blending processes.

The systems described herein relate to blending two streams of varying components to form a blended third stream. The systems may include a first supply line for supplying a first stream at a first flow rate and a second supply line for supplying a second stream at a second flow rate. All or portions of the first and second streams are blended to form the blended third stream. The systems may further include analyzing devices positioned in the first and second supply lines for analyzing the first and second stream compositions. Additionally, measuring devices may be positioned in each of the first and second supply lines for measuring the flow rate of the first and second streams.

FIG. 1 depicts one embodiment of the processes and systems described herein. The system depicted in this embodiment is described in connection with the production of a product stream produced by blending two hydrocarbon-containing streams. However, it is understood that the systems depicted in FIG. 1 and other embodiments described herein, are useful for producing an infinite variety of streams created by blending at least two streams of varying compositions, including non-hydrocarbon streams, with the intent to create a blended stream meeting precise mandated specifications. For example, the processes and systems described herein are useful for blending an oxygen-containing stream into a hydrocarbon stream.

In FIG. 1, line 1 transports a first stream containing propane and, if existent, other hydrocarbon components such as ethane, propylene and/or iso-butane. A meter 3 is used to measure the flow of the first stream through the first line 1. A signal 5 representative of the flow volume of the first stream in the first line 1 is transmitted to a controller 7 which may be any standard digital micro-processor controller such as desktop computer. In one embodiment, the processor is a Seimens programmable logic controller.

The composition of the first stream in the first line 1 is determined through the use of an analysis means such as analysis means 9 positioned in the flow of the first stream in the first line 1. The analysis means 9 may be any of a variety of standard chromatographs, infrared devices or other devices capable of analyzing a hydrocarbon stream and producing a signal representative of component concentrations in the hydrocarbon stream. In one embodiment, the analysis means 9 is any of a variety of suitable chromatographs produced by Daniel. In the embodiment depicted, the analysis means 9 provides an analysis of propane, propylene, iso-butane and ethane concentration in the first stream transported in line 1. A signal 11 representative of the propane, propylene, iso-butane and ethane concentrations in the first stream in line 1 is transmitted to the digital micro-processor controller 7.

A second line 13 transports a second stream containing ethane or an ethane-propane mixture, and optionally other hydrocarbons that may be sourced from storage tank 31. Alternatively, the second stream may be provided from other sources such as a pipeline or processing unit. A meter 15 is used to measure the flow of the second stream through the second line 13. A signal 17 representative of the flow volume of the second stream in the second line 13 is transmitted to the controller 7 described previously. The composition of the second stream in the second line 13 is determined through the use of an analysis means such as a chromatograph 19 positioned in the flow of the second stream in second line 13. The analysis means may be any of a variety of standard chromatographs, infrared devices or other devices capable of analyzing a hydrocarbon stream such as described previously in connection with analysis means 9. In the embodiment depicted, the analysis means 19 provides an analysis of the ethane and propane concentration in the second stream transported in line 13. A signal 21 representative of the ethane and propane concentrations in the second stream in line 13 is transmitted to controller 7.

To blend the first and second streams to produce a third stream, all or a portion of the second stream in line 13 is blended into the first stream in line 1. In one embodiment, the composition of the resultant blended stream is controlled and determined by the flow of all or a portion of the second stream in the second line 13 into the first stream by a controlled opening and closing of valve 23. In particular, the volume of flow of the second stream in line 13 through the control valve 23 into the first stream in line 1 is determined by a signal 25 produced by controller 7. The signal 25 is representative of the flow rate of the second stream through the control valve 23 necessary to produce a desired composition in the stream resulting from blending the volumes of the first and second streams. In the embodiment depicted, the portion 27 of the second stream in line 13 permitted to flow though valve 23 is blended with the first stream in line 1 by introduction into the first stream though a hot tap 29 into line 1.

Figure 2:
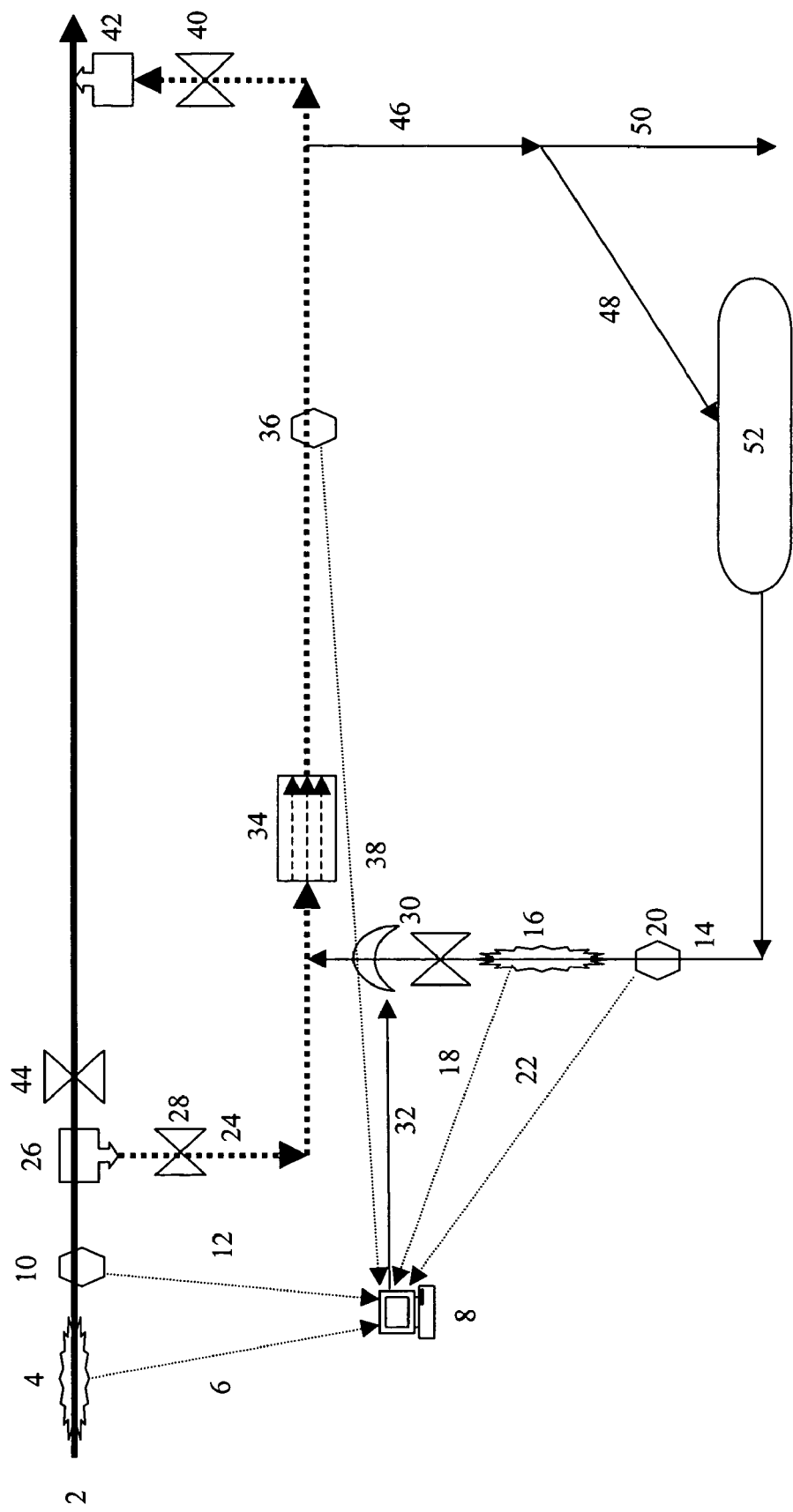
FIG. 2 is a schematic representation of an embodiment of the processes and systems described herein.

FIG. 2 depicts another embodiment of the processes and systems described herein. The system depicted in this embodiment is described in connection with the production of a propane product stream produced by blending two hydrocarbon containing streams. However, it is understood that the system depicted is useful for producing an infinite variety of streams created by blending at least two streams of varying compositions to produce a blended stream meeting precise mandated specifications. In FIG. 2, line 2 transports a first stream containing propane and, if existent, other hydrocarbon components such as ethane, propylene and/or iso-butane. A meter 4 is used to measure the flow of the first stream through the first line 2. A signal 6 representative of the flow volume of the first stream in the first line 2 is transmitted to a controller 8 which may be any standard digital micro-processor controller such as desktop computer. In one embodiment, the processor is a Seimens programmable logic controller. The composition of the first stream in the first line 2 is determined through the use of an analysis means 10 positioned in the flow of the first stream in the first line 2. The analysis means may be any of a variety of standard chromatographs, infrared devices or other devices capable of analyzing a hydrocarbon stream and producing a signal representative of component concentrations in the hydrocarbon stream. In one embodiment, the analysis means 10 is any of a variety of suitable chromatographs produced by Daniel. In the embodiment depicted, the chromatograph 10 provides an analysis of propane, propylene, iso-butane and ethane concentration in the first stream transported in line 2. A signal 12 representative of the propane, propylene, iso-butane and ethane concentrations in the first stream in line 2 is transmitted to a digital microprocessor controller 8.

A second line 14 transports a second stream containing ethane or an ethane-propane mixture, and optionally other hydrocarbons. A meter 16 is used to measure the flow of the second stream through the second line 14. A signal 18 representative of the flow volume of the second stream in the second line 14 is transmitted to the controller 8 described previously. The composition of the second stream in the second line 14 is determined through the use of an analysis means 20 positioned in the flow of the second stream in second line 14. The analysis means may be any of a variety of standard chromatographs, infrared devices or other devices capable of analyzing a hydrocarbon stream such as described previously in connection with chromatograph 10. In the embodiment depicted, the analysis means 20 provides an analysis of the ethane and propane concentration in the second stream transported in line 14. A signal 22 representative of the ethane and propane concentration in the second stream in line 14 is transmitted to controller 8.

To blend the first and second streams to produce a third stream, the first stream may be diverted into a third line 24 through a hot tap 26 and valve 28. The composition of the blended third stream is controlled and determined by the flow of the second stream from the second line 14 into the third line 24 wherein the first and second streams are blended. In the embodiment depicted, the volume of the second stream flowing into the third line 24 to blend with the first stream is controlled through the use of a control valve 30. In particular, the volume of flow of the second stream through the control valve 30 into the third line 24 is determined by a signal 32 produced by controller 8. The signal 32 is representative of the flow rate of the second stream through the control valve 30 necessary to produce a desired composition in the third stream by blending the volumes of the first and second stream entering the third line 24.

After blending of the first stream and the second stream in the third line 24, the composition of the resulting blended third stream is determined by the use of an analysis means such as analysis means 36 positioned in the flow of the third stream in third line 24. The analysis means may be any of a variety of standard chromatographs, infrared devices or other devices capable of analyzing the composition of a hydrocarbon stream such as described previously in connection with chromatograph 10. In the embodiment depicted, the analysis means 36 provides an analysis of the propane, propylene, iso-butane and the ethane concentration in the third stream transported in line 24 downstream of mixer 34. A signal 38 representative of the propane, propylene, iso-butane and the ethane concentration in the third stream in line 24 is transmitted to controller 8.

By programming the controller 8 with a desired concentration of the blended third stream, the controller may be programmed to produce a signal 32 to regulate the opening or closing of the control valve 30 as appropriate to allow the necessary amount of the second stream to enter the third line 24. The appropriate signal 32 to properly regulate control valve 30 is calculated by the controller in response to the signals transmitted to the controller 8 as previously described. In particular, the signal 12 representative of the propane, propylene, iso-butane and the ethane concentration in the first steam; the signal 22 representative of the propane, propylene iso-butane and the ethane concentration in the second steam; the signal 38 representative of the propane, propylene, iso-butane and the ethane concentration in the third stream; the signal 6 representative of the flow volume of the first stream in the first line 4; the signal 18 representative of the flow volume of the second stream are used by the controller to produce the signal 38 to regulate the opening or closing of the control valve 30 as appropriate to allow the necessary amount of the second stream to enter the third line 24.

Once the appropriate volumes of the first and second streams enter the third line 24 to produce the third stream having the desired compositional characteristics, blending of the first and second streams in the third line 24 may be facilitated by any suitable mixing means 34. In the embodiment depicted, the mixing means 34 is a static mixer. A suitable static mixer is available from Kenics under the designation turbulent shear field.

It has been generally determined that the blending of the first and second streams will reach equilibrium to form the blended third stream within a distance of about 10 diameters of the third line 24 following the mixer 34. In other words, if the diameter of the third line is 10 inches, the blended third stream will become fully blended after traveling 100 inches along the third line 24 past mixer 34.

Once the composition of the third stream in the third line 24 is determined through the use of analysis means 36, the third stream may be directed along a variety of routes, depending on the results of the compositional analysis of the third stream. If the third stream meets the targeted specifications for the third stream, the third steam may be directed to the downstream portion of the first line 2 through valve 40 and hot tap 42. Once in the first line 2, the third stream may be directed to any desired destination of the "on-spec" third stream. Of course, it is understood the third stream in the third line 24, produced in accordance with the processes and systems described herein, may be routed to any desired location by any suitable means.

In the embodiment depicted, if it is determined through the use of chromatograph 36 that the third stream in the third line 24 does not meet the desired specifications, valves 28, 30, and 40 may be closed and valve 44 in the first line 2 opened and the third stream directed through a line 46 to either a line 48 or line 50 for alternative uses. In the embodiment depicted, the "off-spec" third stream may be directed through line 48 to a storage tank 52 from which the "off-spec" stream may be used as a source of the second stream 14 for re-blending to produce a new third stream. Alternatively, "off-spec" third stream may be directed through line 50 for disposal in a flaring system (not shown) or other suitable disposal system. In most cases "off-spec" third stream may be blended into the full-flow first stream through valve 40 in the down stream portion of the first line 2.

One of the features of the system depicted in FIG. 2 is the ability to isolate an "off-spec" third stream product while at the same time maintaining functionality of the first line 2. In the event, that the chromatograph 36 detects an "off-spec" third stream product in the third line 24, the system may be programmed to provide a rapid response to prevent "off-spec" product from being directed into the first line 2. For example, if an "off-spec" third stream product is detected, valves 28, 30, and 40 may be closed and valve 44 opened. The "off-spec" product in the third line 24 may then be directed for use as the second stream or for suitable disposal as discussed above. By closing valves 28 and 40 and opening valve 44, the first line 2 may be maintained in service for transport of the first stream to desired designations. For example, the system depicted in FIG. 2 may be used in conjunction with a facility used for the transport and delivery of a propane product stream. The first stream may be an "on-spec" product stream that is normally delivered to customers through the first line 2.

The blending capabilities depicted in FIG. 2 may be used to blend a lower cost ethane component into the propane product first stream while at the same time maintaining the propane product stream within "on-spec" ranges. In the event that the third stream in the third line 24 goes "off-spec" for the propane product stream, the system may be controlled as described above to isolate the "off-spec" propane product stream while at the same time maintain the first line 2 for continued transport of the first stream to customers.

Process control of the processes and systems described herein may be achieved in accordance with a variety of equations that are applicable to the blending of two streams containing an infinite variety of components. In other words, the equations are applicable to control of the processes and systems described herein whether the components in the streams are hydrocarbons, as described in connection with the embodiments previously discussed, or non-hydrocarbon components.

In certain embodiments, at least five signals are generated for use in control equations. Through the use of these signals and process control equations, real-time control of the blending of the first and second streams may be achieved. The at least five signals are as follows: (1) generating a first signal representative of the flow volume of the first stream; (2) generating a second signal representative of the targeted minimum concentration of a first component in the third stream; (3) generating a third signal representative of the concentration of a second component in the first stream; (4) generating a fourth signal representative of the concentration of the second component in the second stream; and (5) using the first signal, the second signal, the third signal, and the forth signals to generate a fifth signal representative of a flow rate of the second stream necessary to produce a desired composition in the third stream produced by blending the first and second streams.

In other embodiments, at least four signals are generated for use in control equations. Through the use of these signals and the process control equations, real-time control of the blending of the first and second streams may be achieved. The least four signals are as follows: (1) generating a first signal representative of the flow volume of the stream; (2) generating a second signal representative of the concentration of a second component in the first stream; (3) generating a third signal representative of the concentration of the second component in the second stream; and (4) using the first signal, the second signal, and the third signal to generate a fifth signal representative of a flow rate of the second stream necessary to produce a desired composition of the third stream produced by blending the first and second streams.

In the specific embodiments depicted in FIG. 1 and FIG. 2, as well as other embodiments not specifically depicted, controllers 7 and 8 may be programmed to produce signals 25 and 32 in accordance with one of the equations outlined below.

To control the concentration of the first component in the blended stream, the following process control equation (A) may be used:

$$V_2 = V_1((TV_{3a} - V_{1a})/(V_{2a} - TV_{3a})) \tag{A}$$

To achieve a specified vapor pressure of the blended stream taking into account a first and a second component, the following process control equation (B) may be used:

$$V_2 = V_1((C_a * V_{1a}) + (C_b * V_{1b})) - TVP)/(TVP - (C_a * V_{2a}) - (C_b * V_{2b})) \tag{B}$$

Alternatively, to achieve a specified vapor pressure of the blended stream, taking into account a first component, a second component, a third component, and a fourth component, the following equation (C) may be employed:

$$V_2 = V_1((C_a * V_{1a}) + (C_b * V_{1b}) + (C_c * V_{1c}) + (C_d * V_{1d}) - VP)/(TVP - (C_a * V_{2a}) - (C_b * V_{2b}) - (C_c * V_{2c}) - (C_d * V_{2d})) \tag{C}$$

In another embodiment, to effectuate a maximum vapor pressure while maintaining minimum content of one of the components in the blended stream, taking into account a first and a second component, the following process control equation may be implemented:

$$V2=V1*((TV3b*V1a)-((1-TV3b)*V1b))/(((1-TV3b)V2b)-(TV3b*V2a)) \quad (D)$$

In still another embodiment, to effectuate a maximum vapor pressure while maintaining minimum content of one of the components in the blended stream, taking into account a first, a second component, a third component, and a fourth component, the following process control equation (E) may be implemented:

$$V2=V1*((TV3b*V1a)+(TV3b*V1c)+(TV3b*V1d)-((1-TV3b)*V1b))/(((1-TV3b)*V2b)-(TV3b*V2a)-(TV3b*V2c)-(TV3b*V2d)) \quad (E)$$

The following abbreviations are applicable to the preceding process control equations (A)-(E):
  Ca=First Component Vapor pressure
  Cb=Second Component Vapor pressure
  Cc=Third Component Vapor pressure
  Cd=Fourth Component Vapor pressure
  V1a=First Stream Volume % First Component
  V1b=First Stream Volume % Second Component
  V1c=First Stream Volume % Third Component
  V1d=First Stream Volume % Fourth Component
  V2a=Second Stream Volume % First Component
  V2b=Second Stream Volume % Second Component
  V2c=Second Stream Volume % Third Component
  V2d=Second Stream Volume % Fourth Component
  TVP=Target Vapor Pressure of Third Stream
  TV3a=Target First Component Content in Third Stream
  TV3b=Target Minimum Second Component Content in Third Stream
  V1=First Stream Volume to be blended
  V2=Second Stream volume to be blended In certain embodiments, the first component may be ethane, the second component may be propane, the third component may be propylene, and the fourth component may be iso-butane.

It has been determined that the processes and systems described herein are useful to achieve very precise and rapid control of a blending system to produce a blended product stream within narrow compositional tolerance levels. Real-time analysis and control is made possible by the generation of digital signals representing the various volume flows and stream compositions as described above. Specifically, the process and systems described herein may be used to generate essentially continuous digital signals to precisely control the blending operations. In one embodiment, the controls are renewed in short intervals. This rapid generation allows the system to operate within narrow tolerances while consistently maintaining an "on-spec" blended product steam.

For example, the product of a blended propane product stream designed to meet commercial LPG specifications requiring that vapor pressure not exceed 208 psig at 100° F. (1.43 MPag at 37.7° C.). The processes and systems described herein may be used to consistently blend "on-spec" commercial LPG blended product streams by targeting a vapor pressure to not exceed 208 psig at 100° F. (1.43 MPag at 37.7° C.). The majority of propane produced in the North America is delivered to the final consumer as HD-5 propane. Industry accepted specification for HD-5 propane includes key specifications of: minimum propane composition of 90 liquid volume percent, maximum propylene composition of 5 liquid volume percent, maximum butane composition of 2.5 liquid volume percent and must not exceed a vapor pressure of 208 psig@100° F. (1.43 MPag at 37.7° C.). This specification allows certain levels of ethane to be included of from 2.5 liquid volume percent to approximately 7.0 liquid volume percent. Propane marketed under non-HD-5 propane specifications could allow for more or less ethane blending. Because of rapid response and control of the processes and systems described herein, it is unnecessary that a wide tolerance range be factored into the targeted blended stream composition to consistently produce an "on-spec" propane product stream. This response and control makes it possible to blend more of the lower value ethane stream into the blended product stream and still achieve "on-spec" product consistently over time.

As noted above, the process control schemes, processes, systems, and equations are applicable to control of the processes and systems described herein whether the components in the streams are hydrocarbons, as described in connection with the embodiments previously discussed, or non-hydrocarbon components.

The processes and systems described herein may also be used to specific blended streams that provide predictable feedstocks for petrochemical facilities that are operationally sensitive to compositional changes in feedstocks.

All patents and publications referred to herein are hereby incorporated by reference in their entireties.

Although the present invention and its advantages have been described in detail, it should be understood that various changes, substitutions, and alterations could be made without departing from the spirit and scope of the invention as defined by the following claims.

The invention claimed is:

1. A method of blending a first stream comprising propane and a second stream comprising ethane to produce a third stream comprising ethane and propane, the method comprising the steps of:
  (i) generating a first signal representative of a flow volume of the first stream;
  (ii) generating a second signal representative of a targeted concentration of ethane in the third stream;
  (iii) generating a third signal representative of the concentration of propane in the first stream;
  (iv) generating a fourth signal representative of the concentration of propane in the second stream; and
  using the first signal, the second signal, the third signal, and the fourth signal to generate a fifth signal representative of a flow rate of the second stream necessary to produce a desired composition comprising ethane and propane in the third stream produced by blending the first and second streams, wherein the first stream comprises at least 90 volume percent propane and has a vapor pressure of about 170 psig at 100° F. to about 186 psig at 100° F., the second stream comprises at least 60 volume percent ethane and has a vapor pressure of about 392 psig at 100° F., to about 785 psig at 100° F., and the third stream has a vapor pressure of about 198 psig at 100° F., to about 208 psig at 100° F.

2. The method of claim 1 wherein the first stream and the second stream are blended by using the fourth signal to control the flow rate of the second stream blended with the first stream to produce the targeted concentration of ethane in the third stream.

3. The method of claim 2 wherein a sixth signal representative of the concentration of ethane in the third stream is generated and the sixth signal is used to compare the concentration of ethane in the third stream with the targeted concentration of ethane in the third stream.

4. The method of claim 2 wherein the first stream and the second stream comprise at least 90 volume % of hydrocarbon components.

5. The method of claim 4 wherein the fifth signal is generated by the following:

$$V2=V1((TV3a-V1a)/(V2a-TV3a))$$

wherein V2 is a volume of the second stream to be blended; V1 is a volume of the first stream to be blended; TV3$a$ is the targeted ethane concentration in the third stream; V1$a$ is the ethane concentration of the first stream; and V2$a$ is the ethane concentration in the second stream.

6. The method of claim 5 wherein the first and second streams are blended with a static mixer.

7. The method of claim 6 wherein the third stream comprises less than 95 liquid volume % propane and at least 4 liquid % ethane.

8. The method of claim 3 wherein the second signal, the third signal, and the sixth signal are generated by a device selected from a chromatograph, an infrared device, and other devices capable of analyzing the composition of a hydrocarbon stream.

9. A method of blending a first stream comprising propane and a second stream comprising ethane to produce a third stream comprising ethane and propane, the method comprising the steps of:
(i) generating a first signal representative of a flow volume of the first stream;
(ii) generating a second signal representative of the concentration of a propane in the first stream;
(iii) generating a third signal representative of the concentration of propane in the second stream; and
using the first signal, the second signal, and the third signal to generate a fourth signal representative of a flow rate of the second stream necessary to produce a desired composition comprising ethane and propane in the third stream produced by blending the first and second streams, wherein the first stream comprises at least 90 volume percent propane and has a vapor pressure of about 170 psig at 100° F. to about 186 psig at 100° F., the second stream comprises at least 60 volume percent ethane and has a vapor pressure of about 392 psig at 100° F. to about 785 psig at 100° F., and the third stream has a vapor pressure of about 198 psig at 100° F. to about 208 psig at 100° F.

10. The method claim 9 wherein the fourth signal is generated by the following:

$$V2=V1((Ca*V1a)+(Cb*V1b))-TVP)/(TVP-(Ca*V2a)-(Cb*V2b))$$

wherein V2 is a volume of the second stream to be blended; V1 is a volume of the first stream to be blended; Ca is the vapor pressure of ethane; V1$a$ is the concentration of ethane in the first stream; Cb is the vapor pressure of propane; V1$b$ is the concentration of propane in the first stream; TVP is a targeted vapor pressure of the third stream; V2$a$ is the concentration of ethane in the second stream; and V2$b$ is the concentration of propane in the second stream.

11. The method of claim 10 wherein the first stream and the second stream comprise at least 90 volume % of hydrocarbon components.

12. The method of claim 11 wherein the third stream comprises less than 95 volume % propane and at least 4 volume % ethane.

13. The method of claim 9 wherein the first stream and the second stream comprise a third component and a fourth component and the fourth signal is generated by the equation:

$$V2=V1((Ca*V1a)+(Cb*V1b)+(Cc*V1c)+(Cd*V1d)-TVP)/(TVP-(Ca*V2a)-(Cb*V2b)-(C-c*V2c)-(Cd*V2d))$$

wherein V2 is a volume of the second stream to be blended; V1 is a volume of the first stream to be blended; Ca is the vapor pressure of the ethane; V1$a$ is an ethane concentration of the first stream; Cb is the vapor pressure of the propane; V1$b$ is the concentration of propane in the first stream; Cc is vapor pressure of the third component; V1$c$ is the third component concentration in the first stream; Cd is the vapor pressure of the fourth component; V1$d$ is the fourth component concentration in the first stream; TVP is a targeted vapor pressure of the third stream; V2$a$ is the ethane concentration in the second stream; V2$b$ is the propane concentration in the second stream; V2$c$ is the third component concentration in the second stream; and V2$d$ the fourth component concentration in the second stream.

14. The method of claim 13 wherein the third component is propylene, and the fourth component is iso-butane.

15. The method claim 9 wherein the fourth signal is generated by the following:

$$V2=V1*((TV3b*V1a)-((1-TV3b)*V1b))/(((1-TV3b)V2b)-(TV3b*V2a))$$

wherein V2 is a volume of the second stream to be blended; V1 is a volume of the first stream to be blended; TV3$b$ is a targeted minimum concentration of the propane in the third stream; V1$a$ is the ethane concentration of the first stream; V1$b$ is the concentration of the propane in the first stream; V2$b$ is the concentration of propane in the second stream; and V2$a$ is the concentration of ethane in the second stream.

16. The method of claim 15 wherein the first stream and the second stream comprise at least 90 volume % of hydrocarbon components.

17. The method of claim 16 wherein the first stream comprises at least 90 liquid volume % propane and the second stream comprises at least 60 liquid volume % ethane.

18. The method of claim 17 wherein the third stream comprises less than 95 liquid volume % propane and at least 4 liquid % ethane.

19. The method of clam 15 wherein the first stream and the second stream comprise a third component and a fourth component and the fourth signal is generated by the equation:

$$V2=V1*((TV3b*V1a)+(TV3b*V1c)+(TV3b*V1d)-((1-TV3b)*V1b))/(((1-TV3b)*V2b)-(-TV3b*V2a)-(TV3b*V2c)-(TV3b*V2d)$$

wherein V2 is a volume of the second stream to be blended; V1 is a volume of the first stream to be blended; TV3$b$ is a targeted minimum propane concentration in the third stream; V1$a$ is the ethane concentration of the first stream; V1$c$ is the third component concentration in the first stream; V1$d$ is the fourth component concentration in the first stream; V1$b$ is propane concentration in the first stream; V2$b$ is the concentration of propane in the second stream; V2$a$ is the concentration of ethane in the second stream; V2$c$ is the third component concentration in the second stream; and V2$d$ the fourth component concentration in the second stream.

20. The method of claim 19 wherein the third component is propylene, and the fourth component is iso-butane.

* * * * *